United States Patent
Kirchmeyer et al.

(10) Patent No.: US 7,196,206 B2
(45) Date of Patent: Mar. 27, 2007

(54) ASYMMETRICAL LINEAR ORGANIC OLIGOMERS

(75) Inventors: Stephan Kirchmeyer, Leverkusen (DE); Sergei Ponomarenko, Moskau (RU); Marcus Halik, Erlangen (DE)

(73) Assignee: H.C. Starck GmbH & Co. KG, Goslar (DE)

( * ) Notice: Subject to any disclaimer, the term of this patent is extended or adjusted under 35 U.S.C. 154(b) by 316 days.

(21) Appl. No.: 10/984,512

(22) Filed: Nov. 9, 2004

(65) Prior Publication Data

US 2005/0139822 A1 Jun. 30, 2005

(30) Foreign Application Priority Data

Nov. 12, 2003 (DE) ................. 103 53 093

(51) Int. Cl.
 C07D 409/00 (2006.01)
 B32B 9/00 (2006.01)
 C08F 2/00 (2006.01)
 C08G 10/02 (2006.01)

(52) U.S. Cl. .................. 549/59; 428/690; 526/220; 528/244

(58) Field of Classification Search ................ 549/59; 428/690; 526/220; 528/244
See application file for complete search history.

(56) References Cited

U.S. PATENT DOCUMENTS

| | | | |
|---|---|---|---|
| 6,414,164 B1 | 7/2002 | Afzali-Ardakani et al. | ... 549/59 |
| 6,433,359 B1 | 8/2002 | Kelley et al. | .............. 257/40 |
| 6,936,190 B2 * | 8/2005 | Yoshida | .................. 252/511 |
| 7,057,054 B2 * | 6/2006 | Irie | .......................... 549/59 |
| 7,102,017 B2 * | 9/2006 | Liu et al. | ................... 549/59 |
| 7,126,013 B2 * | 10/2006 | Heeney et al. | ............. 549/59 |
| 2003/0099845 A1 | 5/2003 | Ogawa et al. | ........... 428/447 |
| 2004/0183069 A1 | 9/2004 | Afzali-Ardakani et al. | ... 257/40 |

OTHER PUBLICATIONS

Database CA Online! Chemical Abstracts Service, Columbus, Ohio, US: Park, Mi-Kyoung et al: "Synthesis of monofunctional and amphiphilic oligothiophenes" XP002316608 gefunden im STN Database accession No. 130:352677 * Zusammenfassung * & Polymeric Materials Science and Engineering, 80, 241-242 Coden: PMSEDG; ISSN: 0743-0515, 1999.
Database CA 'Online! Chemical Abstracts Service, Columbus, Ohio, US; Advincula R.C. et al: "Towards the synthesis of mono- and bi-functional amphiphilic oligothiophenes: organic materials for opto-electronic applications" XP002316609 gefunden im STN Database accession No. 131:351181 * Zusammenfassung * & Materials Research Society Symposium Proceedings, Bd, 561, 1999, Seiten 155-160 ISSN: 0272-9172.
Michalitsch, R. et al: "A practical synthesis of functionalized alkyl-oligothiophenes for molecular self-assembly" Journal of Heterocyclic Chemistry, 39(3), 649-653 Coden: JHTCAD; ISSN: 0022-152X, 2001, XP002316604.
Katz, Howard E. et al: "Synthesis, Solubility, and Field-Effect Mobility of Elongated and Oxa-Substituted .alpha.,.omega.-Dialkyl Thiophene Oligomers. Extension of "Polar Intermediate" Synthetic Strategy and Solution Deposition on Transistor Substrates" Chemistry of Materials, 10(2), 633-638 Coden: CMATEX' ISSN: 0897-4756, 1998, XP002316605.
Afzali, A. et al: An Efficient Synthesis of Symmetrical Oligothiophenes: Synthesis and Transport Properties of a Soluble Sexithiophene Derivative: Chemistry of Materials, 14(4), 1742-1746 Coden: CMATEX; ISSN: 0897-4756, 2002, XP002316606.
Araki, Yasuyuki et al: "Photoinduced Charge Separation and Charge Recombination of Oligothiophene-Viologen Dyads in Polar Solvent" Journal of Physical Chemistry A, 108(48), 10649-10655 Coden: JPCAFH; ISSN: 1089-5639, 2004, XP002316607.
Applied Physics Letters, vol. 73, No. 18, Nov. 2, 1998, pp. 2681-2683, J. Collet et al, "Nano-field effect transistor with an organic self-assembled monolayer as gate insulator".
Applied Physics Letters, vol. 76, No. 14, Apr. 3, 2000, pp. 1941-1943, J. Collet et al, "Low-voltage, 30 nm channel length, organic transistors with a self-assembled monolayer as gate insulating films".
Colloids and Surfaces A, 198-200 (month unavailable) 2002, pp. 577-591, C. Nogues et al, "SAMs functionalised by α-quaterthiophene as model for polythiophene grafting".
J. Phys. Chem. B, 101, (month unavailabl) 1997, pp. 5951-5962, B. Liedberg et al, "Self-Assembly of α-Functionalized Terthiophenes on Gold".
J. Am. Chem. Soc., 120, (month unavailable) 1998, pp. 13453-13460, Anna Berlin et al, "Adsorption of Carboxyl-Terminated Dithiophene and Terthiophene Molecules on ITO Electrodes and Their Electrochemical Coupling to Polymer Layers. The Influence of Molecular Geometry" (Also see Supporting Information attached).
Mat. Res. Soc. Symp. Proc., vol. 708, (month unavailable) 2002, pp. 305-309, Jung F. Kang et al, "Surface Structure and Electrochemical Polymerization of Mixed, Thiophene-Capped Monolayers".

* cited by examiner

*Primary Examiner*—Deborah C. Lambkin
(74) *Attorney, Agent, or Firm*—Connolly Bove Lodge & Hutz LLP

(57) ABSTRACT

The invention relates to asymmetrical linear organic oligomers represented by the following formula (I), $$X-R^1-[Ar]_n-R^2 \qquad (I)$$

in which n is from 4 to 10, Ar is for example an optionally substituted 2,5-thienylene group, $R^1$ is for example a $C_{10}-C_{20}$ alkylene group, $R^2$ is for example a $C_1-C_{12}$ alkyl group, and X is for example a vinyl group or an alkoxysilyl group. Also described is a process for the production of such organic oligomers, and semiconductors in electronic modules that include such organic oligomers.

12 Claims, No Drawings

ASYMMETRICAL LINEAR ORGANIC OLIGOMERS

CROSS REFERENCE TO RELATED PATENT APPLICATION

The present patent application claims the right of priority under 35 U.S.C. § 119 (a)–(d) of German Patent Application No. 103 53 093.2, filed Nov. 12, 2003.

FIELD OF THE INVENTION

The invention concerns asymmetrical linear organic oligomers, a process for their production and their use as semiconductors in electronic modules.

BACKGROUND OF THE INVENTION

The field of molecular electronics has developed rapidly over the last 15 years with the discovery of organic conductive and semiconductive compounds. Over this time many compounds have been found that display semiconductive or electro-optical properties. Semiconductive organic compounds are currently being developed for applications such as organic field effect transistors (OFETs), organic light-emitting diodes (OLEDs), sensors and photovoltaic elements. A field effect transistor is a three-electrode element in which the conductivity of a thin conducting channel between two electrodes (known as "source" and "drain") is controlled by means of a third electrode (known as "gate"), which is separated from the conducting channel by a thin insulating layer. The most important characteristic properties of a field effect transistor are the mobility of the charge carriers, which decisively determine the switching speed of the transistor, and the ratio between the currents in the switched and unswitched state, known as the "on/off ratio". Another important property of a field effect transistor is the inception voltage at which a measurable current starts to flow between source and drain. This voltage is also known as the threshold voltage. Low threshold voltages are generally desirable. In order to reduce this threshold voltage, developers try to make the insulating layer between the gate and the conducting channel as thin as possible.

The thinnest possible insulating layers can be produced from so-called "self-assembled monolayers" (SAMs). Examples of suitable molecules from which SAM layers can be produced are long linear alkanes having more than 10 carbon atoms, which can be anchored to the supporting material of the transistor by means of suitable functional groups in the molecule. U.S. Pat. No. 6,433,359 B1 describes the use of linear, branched or cycloaliphatic hydrocarbons having polar groups, such as e.g. chlorosilyl, carboxyl, hydroxyl, amino, amido and thiol groups, for the production of field effect transistors containing SAM layers between the insulating layer and the semiconductor layer to improve the on/off ratio, threshold voltage (i.e. the voltage at the gate at which a measurable current starts to flow between source and drain), and the mobility of the charge carriers. The use of SAM layers containing thiol groups with a similar objective is described in U.S. Pat. No. 6,335,539 B1.

However, the best properties have been found in field effect transistors in which layers made from SAM molecules are used as the sole insulating layer. For example, field effect transistors that display a current between source and drain at a threshold voltage of 1–2 V have been produced with an approximately 2 nm thin SAM insulating layer consisting of alkyl trichlorosilanes (see, e.g., J. Collet et al., Appl. Phys. Lett. 1998, Vol. 73, No. 18, 2681–2683 and Appl. Phys. Lett. 2000, Vol. 76, No. 14, 1941–1943).

The disadvantage of alkyl-containing SAM layers, however, is that they are difficult to structure and because of the low surface voltage of approximately 20 to 30 mN/m they cause difficulties when it comes to applying additional layers to these layers (e.g., by the wet process). By means of functionalisations, for example of one end of the SAM molecule, with carboxyl groups for example, the surface voltage was able to be increased to around 50 mN/m (see, e.g., Appl. Phys. Lett. 2000, Vol. 76, No. 14 p. 1941–1943).

Linking the alkyl(ene) chains in the SAM molecule to semiconductive, conjugated oligomers, such as oligothiophenes for example, also made it possible to achieve an improvement in the surface voltage between the insulating layer and the semiconductive layer on the one hand and an ordered construction of two layers, the dielectric and the semiconductive layer, in one step on the other. However, although such SAM molecules with oligothiophenes at one end and thiol groups at the other end of an alkylene group had already been described, such as 12-(2,2':5',5",2"'-quaterthien-5-yl)dodecanethiol (see, e.g., Colloids Surf. A, 198–200 (2002) 577–591) or 11-(2,2':5',2"-terthien-5-yl) undec-1-ylthiol (see, e.g., Bäuerle et al., J. Phys. Chem. B 1997, Vol. 101, No. 31, 5951–5962), it is known that compounds containing thiol groups have the disadvantage in the production of SAM layers that they can only be anchored to gold surfaces.

Berlin and Zotti et al. (J. Am. Chem. Soc. 1998, B.120, p. 13453–13460) describe carboxyalkyl-substituted dithiophenes and terthiophenes which are suitable for forming monolayers on indium-tin-oxide layers (ITO). The disadvantage of these compounds, however, lies in the fact that dithiophenes and terthiophenes display no semiconductive properties and are typically only suitable as intermediates for other reactions. Thus dithiophenes or terthiophenes have been polymerised by oxidation after being applied as a layer, for example, but doped conductive polymers were obtained in this way that display no semiconductor effect. The molecules described therein are thus unsuitable as semiconductors both before and after polymerisation.

Other SAM compounds functionalised with a thiophene, pyrrole or other aromatic rings at the end of the molecule, such as e.g. 11-(3-thienyl)undecyl trichlorosilane (Mat. Res. Soc. Symp. Proc. 2002, B.708, p. 305–309) or similar compounds (US-A 2003/0,099,845) have been described. However, these compounds likewise display no semiconductive properties. Following oxidative polymerisation they form electrically conductive polymer layers anchored to the substrate, such as e.g. polypyrrole, polythiophene, polyacetylene and polydiacetylene layers, which are in the oxidised, electrically conductive form and not in the neutral, semiconductive form, however.

There is therefore still a need for SAM molecules that are suitable both (i) for the formation of thin insulating layers on suitable substrates and, (ii) for the formation of semiconductive layers.

SUMMARY OF THE INVENTION

Surprisingly it has been found that semiconductive oligomers carrying a linear alkylene chain substituted with a suitable polar group are particularly suitable for this purpose.

Within the context of the invention, oligomers are understood to be compounds having 2 to 15, preferably 3 to 13, particularly preferably 4 to 10 monomer units (referred to below as Ar units), which can be the same or different.

The present invention provides compounds having the general formula (I),

  (I)

wherein n stands for a whole number from 4 to 10, preferably a whole number from 4 to 8, particularly preferably a whole number from 4 to 6, Ar stands for, independently for each n, optionally substituted 1,4-phenylene, 2,7-fluorenylene, 2,5-thienylene or 1,2-ethenylene, preferably for optionally substituted 2,5-thienylene, $R^1$ stands for a $C_3$–$C_{30}$ alkylene group optionally interrupted by one or more O or S atoms, silylene, phosphonoyl or phosphoryl groups, preferably for a $C_{10}$–$C_{20}$ alkylene group, $R^2$ stands for H or a linear or branched $C_1$–$C_{20}$ alkyl group, preferably a $C_1$–$C_{12}$ alkyl group, or a linear $C_1$–$C_{20}$ alkyl group optionally interrupted by one or more O or S atoms, silylene, phosphonoyl or phosphoryl groups, preferably $C_1$–$C_{12}$ alkyl group, and X stands for a group selected from an optionally substituted vinyl group, a chlorine, iodine, hydroxyl, alkoxy group having 1 to 3 carbon atoms, alkoxysilyl, silyl, chlorosilyl, siloxane, hydroxy, carboxy, methyl or ethyl carbonate, aldehyde, methyl carbonyl, amino, amido, sulfone, sulfonic acid, halosulfonyl, sulfonate, phosphonic acid, phosphonate, trichloromethyl, tribromomethyl, cyanate, isocyanate, thiocyan ate, isothiothiocyanate, cyano or nitro group.

DETAILED DESCRIPTION OF THE INVENTION

According to the invention the n Ar units in the general formula (I) can be the same or different and can be linked together in any order. The n Ar units form a conjugated oligomer chain. In preferred embodiments, in addition to 1,4-phenylene, 2,7-fluorenylene and/or 2,5-thienylene, Ar can also stand for 1,2-ethenylene units, through which the conjugation length is not reduced. For Ar the compounds according to the invention having the general formula (I) preferably contain optionally substituted 2,5-thienylene units or optionally substituted 2,5-thienylene units and optionally substituted 1,4-phenylene units, wherein the substituents that are optionally present can be the same or different. Where optionally substituted 2,5-thienylene units and optionally substituted 1,4-phenylene units are included, such new compounds containing no adjacent optionally substituted 1,4-phenylene units are particularly preferred. Most particularly preferred are compounds having the general formula (I) which contain only 2,5-thienylene units for Ar.

Suitable examples of substituents for Ar include linear or branched $C_1$–$C_{20}$ alkyl radicals, preferably $C_1$–$C_{12}$ alkyl radicals, or linear $C_1$–$C_{20}$ alkyl radicals interrupted by one or more O atoms. In the 2,7-fluorenylene units, substituents that are optionally present (one or more, preferably two) are preferably seated at the 9-position. Particularly preferred substituents for 2,5-thienylene or 1,4-phenylene units are methyl, ethyl, propyl, butyl, pentyl or hexyl groups. Other particularly preferred substituents for 1,4-phenylene units are methoxy, ethoxy, propoxy, butoxy, pentoxy, hexyloxy or heptyloxy groups. The most particularly preferred substituent is hydrogen.

Preferred examples of $R^1$ that can be cited include decylene, undecylene, dodecylene, terdecylene, hexadecylene or octadecylene groups. Preferred examples of $R^2$ that can be cited include methyl, ethyl, propyl, butyl, pentyl, hexyl, heptyl, octyl, nonyl, decyl, undecyl or dodecyl groups. Ethyl or hexyl groups are most particularly preferred.

Suitable examples of groups X in the general formula (I) are preferably optionally substituted vinyl groups, chlorine, iodine, hydroxyl, alkoxy groups having 1 to 3 carbon atoms, alkoxysilyl, silyl, chlorosilyl, siloxane, hydroxy, carboxy, methyl or ethyl carbonate, aldehyde, methyl carbonyl, amino, amido, sulfone, sulfonic acid, halosulfonyl, sulfonate, phosphonic acid, phosphonate, trichloromethyl, tribromomethyl or cyanate, isocyanate, thiocyanate, isothiothiocyanate, cyano or nitro groups. These groups are polar, so they can interact chemically or physically with the substrate, or can easily be converted into polar form. Preferred examples are vinyl, alkoxysilyl, chlorosilyl, siloxane, hydroxy, carboxy, amino or amido groups. Vinyl and alkoxysilyl, siloxane or chlorosilyl groups are particularly preferred. Within the context of the invention alkoxysilyl groups can be mono-, di- or tri-$C_1$–$C_{20}$ alkoxysilyl groups, and siloxane groups can be di-, oligo- or polysiloxanes synthesised from mono-, di- or trifunctional units. Vinyl, trimethoxysilyl, triethoxysilyl groups or alkyl disiloxane groups, such as a tetraalkyl disiloxane group, for example, are most particularly preferred.

Preferred new compounds having the general formula (I) are those having the general formula (I-a),

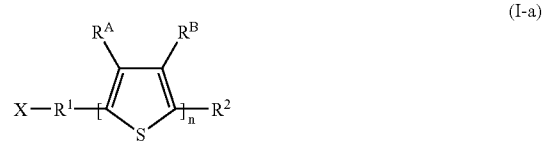 (I-a)

wherein $R^A$, $R^B$ mutually independently stand for H or an optionally substituted linear or branched $C_1$–$C_{20}$ alkyl group, optionally interrupted by 1 to 5 oxygen atoms, preferably for a $C_1$–$C_{12}$ alkyl group, particularly preferably for a methyl, ethyl, propyl, butyl, pentyl or hexyl group, an optionally substituted $C_1$–$C_{20}$ alkoxy group, preferably for a $C_1$–$C_6$ alkoxy group, particularly preferably for a methoxy group, or together stand for an optionally substituted $C_1$–$C_6$ dioxyalkylene group, preferably for a 3,4-ethylenedioxy group, and n, X, $R^1$ and $R^2$ have the meaning cited above for the general formula (I).

In preferred embodiment of the present invention $R^A$ and $R^B$ stand for H.

Other preferred new compounds having the general formula (I) are those in which X stands for a vinyl group.

In a preferred embodiment of the present invention these are such compounds having the general formula (I-a-1),

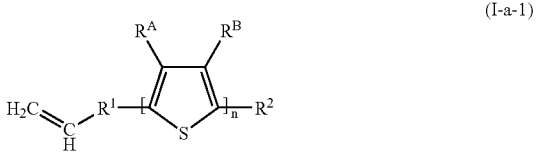

(I-a-1)

wherein n, X, $R^1$ and $R^2$ have the meaning cited above for the general formula (I) and $R^A$ and $R^B$ having the meaning cited above for the general formula (I-a).

Other preferred compounds having the general formula (I) are those wherein X stands for an alkoxysilyl group, in particular a mono-, di- or tri-$C_1$–$C_{20}$ alkoxysilyl group, such as e.g. trimethoxysilyl or triethoxysilyl, or a siloxane group, in particular a tetraalkyl disiloxane group.

In a further preferred embodiment of the invention, compounds having the general formula (I) wherein X stands for an alkoxysilyl group are compounds having the general formulae (I-a-2),

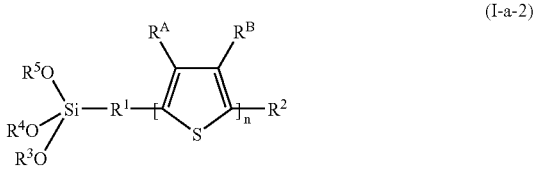

(I-a-2)

wherein
$R^3$, $R^4$ and $R^5$ mutually independently stand for H or a linear or branched $C_1$–$C_{20}$ alkyl group, preferably $C_1$–$C_6$ alkyl group, particularly preferably methyl or ethyl, and
n, $R^1$ and $R^2$ have the meaning cited above for the general formula (I) and $R^A$ and
$R^B$ have the meaning cited above for the general formula (I-a).

In preferred embodiments of the present invention compounds having the general formula (I) wherein X stands for a siloxane group are compounds having the general formulae (I-a-3),

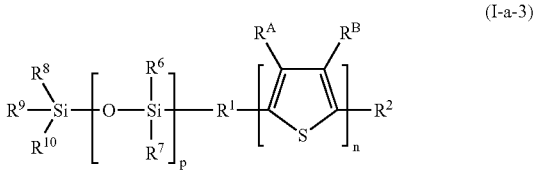

(I-a-3)

wherein
$R^6$ to $R^{10}$ mutually independently stand for H or a linear or branched $C_1$–$C_{20}$ alkyl group, preferably $C_1$–$C_6$ alkyl group, particularly preferably methyl or ethyl,
p stands for a whole number from 1 to 5, preferably for 2 or 3, particularly preferably for 2, and
n, $R^1$ and $R^2$ have the meaning cited above for the general formula (I) and $R^A$ and $R^B$ have the meaning cited above for the general formula (I-a).

In principle the compounds according to the invention can be produced by various methods known in principle to the person skilled in the art, such as e.g. by coupling Grignard compounds with monohaloaryl compounds in the presence of nickel (Synthesis 1993, p. 1099–1103) or palladium (Chem. Mater. 1993, B.5, p. 430–436) catalysts. These methods of synthesis lead to compounds that can only be purified with difficulty and at great expense, however, which means that the resulting end products are poorly suited for use as semiconductors.

The compounds according to the invention are preferably produced by means of a variant of the Suzuki coupling, frequently also known as Suzuki condensation. The Suzuki condensation or Suzuki coupling, i.e. the reaction of aryl halides and aryl boric acid compounds with a Pd compound as catalyst in the presence of a base, is described for example in Suzuki et al., Chem. Rev. 1995, 95, 2457–2483. In a preferred embodiment the process is performed according to a variant of this Suzuki coupling, wherein aryl or heteroaryl halides and thiophene pinacolone boric acid esters are reacted, optionally in the presence of at least one base and/or at least one catalyst which contains a metal from subgroup VIII of the periodic table, referred to below as a metal of subgroup VIII for short.

The present invention therefore also provides a process wherein an organoboron compound is reacted with an aryl or heteroaryl halide by means of Suzuki coupling.

This is preferably a process wherein as organoboron compound a compound having the general formula (II),

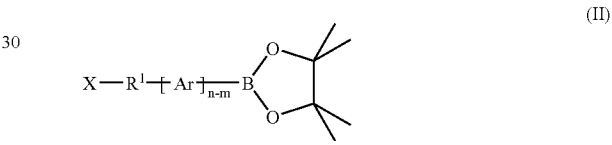

(II)

wherein n, Ar, $R^1$ and X have the meaning cited above for the general formula (I) and m stands for a whole number from 1 to 5, preferably 1 to 4, particularly preferably 2, 3 or 4,
and as aryl or heteroaryl halide a compound having the general formula (III),

(II)

wherein m and Ar have the meaning cited for the general formula (II) and $R^2$ the meaning cited above for formula (I) and Y stands for Cl, Br, I or —O—$SO_2$—$R^3$, wherein $R^3$ stands for a methyl, trifluoromethyl, phenyl or tolyl group, are used and reacted together.

This process variant is most particularly preferably used for the production of new compounds having the general formula (I-a-1), which can then be reacted by further modification at the double bond to other new compounds having the general formula (I-a), preferably to those having the general formulae (I-a-2) or (I-a-3).

The preferred process variant for the production of the new compounds (Suzuki coupling) is performed at a temperature from +20° C. to +200° C., preferably from +40° C. to +150° C., particularly preferably from +80° C. to +130° C., in an organic solvent or solvent blend.

Suitable catalysts containing a metal from subgroup VIII are in principle all suitable compounds containing a metal from subgroup VIII, preferably Pd, Ni or Pt, particularly preferably Pd. The catalyst(s) is/are preferably used in quantities of 0.05 wt. % to 10 wt. %, particularly preferably 0.5 wt. % to 5 wt. %, relative to the total weight of the compounds to be coupled.

Particularly suitable catalysts are complex compounds of metals from subgroup VIII, in particular complexes of palladium(0) which are stable in air, Pd complexes which can easily be reduced with organometallic reagents, such as e.g. lithium alkyls or organomagnesium compounds, or phosphines to palladium(0) complexes, or palladium(2) complexes optionally with addition of $PPh_3$, or other phosphines. For example, $PdCl_2(PPh_3)_2$, $PdBr_2(PPh_3)_2$ or $Pd(OAc)_2$ or mixtures of these compounds with addition of $PPh_3$ can be used. $Pd(PPh_3)_4$, with or without addition of phosphines, in a preferred embodiment without addition of phosphines, is preferably used, which is available in an inexpensive form. $PPh_3$, $PEtPh_2$, $PMePh_2$, $PEt_2Ph$ or $PEt_3$ are preferably used as phosphines, particularly preferably $PPh_3$.

Palladium compounds without addition of phosphine can also be used as catalysts, however, such as e.g. $Pd(OAc)_2$.

Examples of bases that are used are hydroxides, such as e.g. NaOH, KOH, LiOH, $Ba(OH)_2$, $Ca(OH)_2$, alkoxides, such as e.g. NaOEt, KOEt, LiOEt, NaOMe, KOMe, LiOMe, alkali metal salts of carboxylic acids and carbonic acid, such as e.g. sodium, potassium or lithium carbonate, hydrogen carbonate, acetate, citrate, acetyl acetonate, glycinate, or other carbonates, such as e.g. $Cs_2CO_3$ or $Tl_2CO_3$, phosphates, such as e.g. sodium phosphate, potassium phosphate or lithium phosphate, or mixtures thereof. Sodium carbonate is preferably used. The bases can also be used as solutions in water or as suspensions in organic solvents, such as toluene, dioxan or DMF. Solutions in water are preferred, since the products obtained can be easily separated from the reaction mixture because of their low solubility in water.

Other salts, such as e.g. LiCl or LiBr, can also be used as auxiliary substances.

Suitable examples of organic solvents are in principle all solvents or solvent blends which do not react with boric acid esters. These are generally compounds which display no halogen atoms or no hydrogen atoms that react with thiophene pinacolone boric acid esters. Examples of suitable solvents are alkanes such as pentane, hexane and heptane, aromatics such as benzene, toluene and xylenes, compounds containing ether groups such as dioxan, dimethoxyethane and tetrahydrofuran and polar solvents such as dimethylformamide or dimethylsulfoxide. In the process according to the invention aromatics are preferably used as solvent. Toluene is most particularly preferred. Blends of two or more of these solvents can also be used as solvent.

The reaction mixture is recovered by methods known per se, e.g. by dilution, precipitation, filtration, extraction, washing, recrystallisation from suitable solvents, chromatography and/or sublimation. It can be recovered, for example, by pouring the reaction mixture on completion of the reaction into a mixture of acid (ice) water, produced from 1 molar hydrochloric acid for example, and toluene, separating off the organic phase, washing with water, filtering off the product obtained as a solid, washing with toluene and then drying in vacuo. The compounds having the general formula (I) can be obtained in a high quality and purity without any subsequent purification processes and are semiconductive. These products can also be purified further, however, by known processes, e.g. by recrystallisation, chromatography or sublimation.

With this process the compounds according to the invention can be produced without complex purification processes with only very small amounts of impurities. In particular, with this process the compounds according to the invention are obtained largely free from homologous oligomers having a higher or lower molecular weight, which are difficult to separate, thus avoiding the need for a complex purification of mixtures that are difficult to separate.

The organoboron compounds and aryl or heteroaryl compounds used in this process, in particular having the general formula (III), can be produced by known methods or are commercially available. The production of pinacolone boric acid esters having the general formula (II) is described for example in Feast et al., J. Mater. Chem. 2003, 13, 1269–1273.

The new compounds having the general formula (I), in particular (I-a) and (I-a-2) to (I-a-3) are extremely suitable—not least because of their high purity—for the production of semiconductive layers in electronic components, such as e.g. field effect transistors, organic light-emitting diodes, photovoltaic cells, lasers or sensors. In particular, the new compounds having the general formula (I), wherein X stands for an alkoxysilyl group or a siloxane group, preferably the compounds having the general formulae (I-a-2) and (I-a-3), are suitable for the production of monolayers, in particular self-assembled monolayers (SAMs), for field effect transistors. Thus the new compounds having the general formula (I), wherein X stands for an alkoxysilyl group or a siloxane group, preferably the compounds having the general formulae (I-a-2) and (I-a-3), are preferably suitable for the production of semiconductive monolayers, but particularly preferably such monolayers containing both a thin dielectric layer (isolating layer) and a thin semiconductive layer. Other semiconductive layers can also be applied to the thin semiconductive layer. It is also possible, with the aid of the new compounds having the general formula (I), wherein X stands for an alkoxysilyl group or a siloxane group, preferably with the aid of the compounds having the general formulae (I-a-2) and (I-a-3), to produce such layers that lie between a dielectric layer and another semiconductive layer. This can be advantageous, since such an interlayer improves the quality of the semiconductive layer above it, through better contact between the semiconductive and dielectric layer for example. This results for example in improved properties in field effect transistors, such as e.g. increased charge carrier mobility, higher on/off ratio and lower inception voltage.

The present invention therefore also provides the use of the compounds according to the invention for the production of semiconductive layers for electronic components, preferably the use of new compounds having the general formula (I), wherein X stands for an alkoxysilyl group or a siloxane group, particularly preferably of compounds having the general formulae (I-a-2) and (I-a-3), for the production of monolayers which contain both a dielectric layer (insulating layer) and a semiconductive layer. The compounds having the general formulae (I-a-2) and (I-a-3) can most particularly preferably be used to form self-assembled layers (SAMs), i.e. as so-called SAM molecules.

Compounds having the general formula (I), wherein X stands for an alkoxysilyl group or a siloxane group, particularly preferably compounds having the general formulae (I-a-2) and (I-a-3), can be anchored particularly well to substrates or surfaces consisting substantially of silicon or oxidic materials such as e.g. $SiO_2$, $Al_2O_3$, $ZrO_2$, $HfO_2$ or $Ta_2O_5$. The anchoring to these substrates or surfaces takes place with the silyl or siloxane group-carrying end of the new compounds. In comparison to known thiol group-containing SAM molecules, the compounds according to the invention thus have the advantage of being able to be anchored to surfaces other than expensive gold surfaces. Applications other than those for the known thiol group-containing SAM molecules are thus accessible to the compounds according to the invention.

The new compounds having the general formula (I), wherein X stands for a vinyl radical, in particular the compounds having the general formula (I-a-1), can be further modified at the double bond with the aid of simple chemical reactions which are known per se to the person skilled in the art.

Examples of such chemical reactions for the modification of these preferred compounds are in particular reactions in which the $CH_2$=CH— double bond is modified selectively and exclusively, but the other part of the compound is not modified. Examples of such chemical reactions that can be cited are polymerisation, oxidation, addition or substitution reactions. Addition and polymerisation reactions are preferred, with hydrosilylation reactions being particularly preferred.

Producing a compound having the general formula (I) in which X stands for a vinyl group in a first step, and in a second step converting it to a compound having the general formula (I) in which X has a meaning other than vinyl, can be advantageous in particular in cases in which the group X which has a meaning other than vinyl is a group which is unstable under the reaction conditions of the Suzuki coupling. This is the case for example with chlorosilane groups, alkoxysilane groups or siloxane groups. Since the ethenyl group is stable under the reaction conditions of the Suzuki coupling and can be modified accordingly by simple reactions mentioned above and generally known to the person skilled in the art, this route is preferred in particular for the production of new compounds having the general formula (I), wherein X stands for an alkoxysilyl or siloxane group, preferably those having the general formulae (I-a-2) or (I-a-3).

Hydrosilylations and their performance are known to the person skilled in the art. For the modification of the new compounds having the general formula (I), wherein X stands for a vinyl radical, in particular the compounds having the general formula (I-a-1), the hydrosilylation is preferably performed at a temperature of +20° C. to +200° C., preferably +30° C. to +120° C., particularly preferably +60° C. to +90° C., in an organic solvent or solvent blend with a metal-containing catalyst.

Various metal complexes, particularly of metals from subgroup VIII of the periodic table, can be used as metal-containing catalyst, such as e.g. complexes of Rh, Ir, Ni, Co, Pd, Pt and Ru. Preferred catalysts for the hydrosilylation are Pt complexes, such as $H_2PtCl_6$, for example, e.g. in isopropanol (Spier catalyst), and $Pt_2\{[(CH_2=CH)Me_2Si]_2O_3\}$ or similar compounds having a different metal-ligand ratio (Karstedt catalysts). Also preferred are platinum cyclovinyl methyl siloxane complexes comprising cyclic methylvinyl siloxanes or platinum divinyl tetramethyl siloxane complexes in xylene, which are commercially obtainable. Suitable quantities of Pt catalyst are from 1 ppm to 1000 ppm, preferably from 5 ppm to 100 ppm, particularly preferably from 10 to 50 ppm of platinum, relative to the total weight of the reaction mixture.

In principle, all solvents or solvent blends which readily dissolve the compounds having the general formula (I), wherein X stands for a vinyl radical, in particular the new compounds having the general formula (I-a-1), at the reaction temperature are suitable as organic solvents for the hydrosilylation. Suitable solvents are for example alkanes such as hexane and heptane, aromatics such as benzene, toluene and xylenes, and compounds containing ether groups such as dioxan, dimethoxyethane and tetrahydrofuran. Aromatic solvents are preferably used in the new process. Toluene is most particularly preferred. Blends of two or more of these solvents can also be used as solvent, however.

The new compounds having the general formula (I), wherein X stands for a vinyl radical, in particular the compounds having the general formula (I-a-1), are therefore suitable both for the production of compounds which are suitable for forming self-assembled monolayers, or SAMs, and for the production of semiconductive layers for electronic components, in particular SAM layers.

The present invention therefore also provides the use of the new compounds having the general formula (I), wherein X stands for a vinyl radical, in particular the compounds having the general formula (I-a-1), for the production of semiconductive layers for electronic components, in particular SAM layers, and the use of the new compounds having the general formula (I), wherein X stands for a vinyl radical, in particular the compounds according to the invention having the general formula (I-a-1), for the production of compounds which are suitable for forming self-assembled monolayers or SAMs.

To be used for the production of semiconductive layers, the new compounds having the general formulae (I), (I-a) or (I-a-1) to (I-a-3) are preferably applied in the form of layers to suitable substrates, for example to silicon wafers, polymer films or glass plates provided with electrical or electronic structures. All application methods known to the person skilled in the art can be used in principle for the application. For example, the compounds according to the invention can be applied from the gas phase or from solution, the solvent being subsequently evaporated. Application from solution can be performed by the known methods, for example by spraying, dipping, printing and knife application, spin coating and by ink-jet printing. The compounds according to the invention are preferably applied from the liquid phase, e.g. by spin coating from a suitable solvent, e.g. toluene.

The present invention therefore also provides layers, preferably consisting substantially of compounds having the general formula (I), in particular (I-a) or particularly preferred (I-a-1) to (I-a-3).

These are preferably monolayers, particularly preferably SAMs (self-assembled monolayers), i.e. those produced from self-assembled compounds according to the invention.

In preferred embodiments these are layers consisting of compounds having the general formula (I), wherein X stands for an alkoxysilyl or siloxane group, in particular of compounds having the general formula (I-a-2) or (I-a-3), which in particularly preferred embodiments form monolayers which contain both a dielectric layer (insulating layer) and a semiconductive layer.

The layers according to the invention can be further modified after application, for example by heat treatment, e.g. by being passed through a liquid crystalline phase, or for structuring, e.g. by laser ablation.

The layers according to the invention produced from the compounds according to the invention are characterised by high purity and consequently by low defects. In particular, SAMs, i.e. layers produced from self-assembled compounds according to the invention, preferably those having the general formula (I-a-2) or (I-a-3), have the advantage that they easily form both a dielectric layer and a semiconductive layer that are extremely thin, i.e. in molecular dimensions of at most a few nanometers, preferably in monomolecular dimensions. The threshold voltage of a field effect transistor, for example, can be reduced through the use of such SAMs.

The layers according to the invention are suitable for use in active and light-emitting electronic components such as field effect transistors, organic light-emitting diodes, photovoltaic cells, lasers or sensors.

The present invention therefore also provides such electronic components containing at least one of the layers according to the invention.

EXAMPLES 5-(10-Undecenyl)-2,2'-bithiophene, 5-bromo-5'-ethyl-2,2'-bithiophene and 5-bromo-5"-ethyl-2,2':5',2"-terthiophene were produced by known processes (Synthesis, 1993, p. 1099; Chem. Mater., 1993, Vol. 5, p. 430; J. Mater. Chem. 2003, Vol. 13, p. 197).

Before use all reaction vessels were heated by the conventional protective gas method and flooded with nitrogen.

Example 1

Production of 4,4,5,5-tetramethyl-2-[5'-(10-undecenyl)-2,2'-bithien-5-yl]-1,3,2-dioxaborolane (II-a)

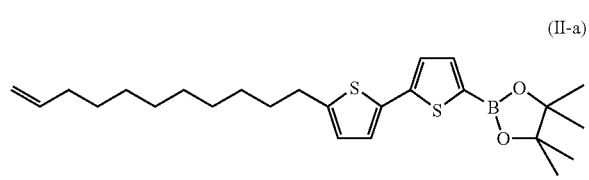

(II-a)

70 ml of anhydrous tetrahydrofuran (THF) were cooled with dry ice/acetone to −74° C. 5.6 ml of a 2.5 M butyl lithium solution in hexane were added dropwise with a syringe. A homogeneous mixture of 5-(10-undecenyl)-2,2'-bithiophene (4.46 g, 14 mmol) in 120 ml of anhydrous THF was then added dropwise and the mixture stirred for 30 min at −74° C. The cooling bath was removed so that the temperature rose. At approx. 0° C. the reaction batch was cooled again and at −74° C. 2-isopropoxy-4,4,5,5-tetramethyl-1,3,2-dioxaborolane (3.3 ml, 16 mmol) was added with a syringe. The mixture was stirred for 30 min at −74° C., the cooling bath removed again and the temperature allowed to rise to 20° C. The reaction mixture was poured into 200 ml of ice-cold water—mixed with 15 ml of 1 M HCl—and extracted with 500 ml of diethyl ether. The ether phase was separated off, washed with water, dried over $Na_2SO_4$, filtered, and the solvent removed entirely in a rotary evaporator. Yield: 6.03 g (97% of theoretical), dark blue, crystalline (II-a).

GC MS analysis: M.+ 99%, m/e=444.

$^1$H NMR (CDCl$_3$, TMS/ppm): 1.22–1.45 (overlapped peaks with a max. at 1.283, 14H), 1.345 (s, 12 H), 1.672 (m, J=7.5 Hz, M=5, 2H), 2.037 (q, J=7.2 Hz, 2H), 2.781 (t, J=7.3 Hz, 2H), 4.928 (d, J=10.3 Hz, 1H), 4.991 (d, J=17.1 Hz, 1H), 5.811 (m, 1H), 6.676 (d, J=3.4 Hz, 1H), 7.037 (d, J=3.9 Hz, 1H), 7.152 (d, J=3.9 Hz, 1H), 7.496 (d, J=3.4 Hz, 1H).

Example 2

Production of 5-ethyl-5'''-(10-undecenyl)-2,2':5',2":5",2'''-quaterthiophene (I-a-1.1)

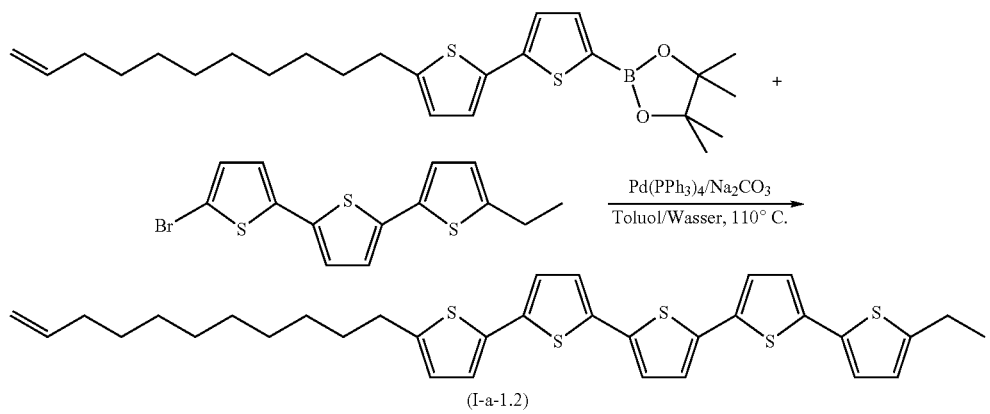

(I-a-1.2)

5-Bromo-5'-ethyl-2,2'-bithiophene (3.28 g, 12 mmol) was measured out and tetrakis(thiphenylphosphine)palladium Pd(PPh$_3$)$_4$ (675 mg, 0.6 mmol) added under protective gas. A solution of 4,4,5,5-tetramethyl-2-[5'-(10-undecenyl)-2,2'-bithien-5-yl]-1,3,2-dioxaborolane (I-a) (6.01 g, 12 mmol) in 120 ml of anhydrous toluene and 18 ml of a 2 M aqueous Na$_2$CO$_3$ solution was prepared and deoxidised with nitrogen. The two solutions were introduced into the reaction batch one at a time by injection, and the reaction mixture was then refluxed for 20 hours. After being cooled, the reaction mixture was poured into a mixture of 200 ml of water, 80 ml of 1 M HCl and 300 ml of toluene. The organic phase was separated off, washed with water, dried over MgSO$_4$, filtered and the solvent removed entirely in a rotary evaporator. The olive green, solid product was recrystallised in n-hexane. Yield: 4.18 g (68% of theoretical) of yellow powder (I-a-1.1).

FD MS analysis: M.+ 100%, m/e=510.0

$^1$H NMR (CDCl$_3$, TMS/ppm): 1.23–1.44 (overlapped peaks with max. at 1.288, 15 H, including t at 1.326 ppm, J=7.6, 3H), 1.680 (m, J=7.5, M=5, 2H), 2.040 (q, J=7.5, 2H), 2.789 (t, J=7.6, 2H), 2.840 (q, J=7.2, 2H), 4.928 (d, J=10.3, 1H), 4.989 (d, J=17.1, 1H), 5.813 (m, 1H), 6.679 (d, J=3.4, 1H), 6.699 (d, J=3.4, 1H), 6.98 (overlapped peaks, 4H), 7.030 (d, J=3.4, 2H).

Example 3

Production of 5-ethyl-5""-(10-undecenyl)-2,2':5',2":5",2'":5"',2""-quinquethiophene (I-a-1.2)

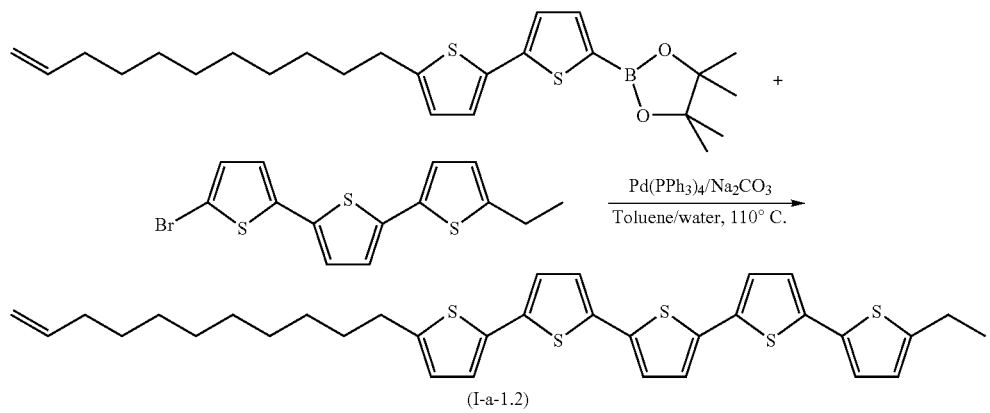

(I-a-1.2)

5-Ethyl-5""-(10-undecenyl)-2,2':5',2":5",2'":5"',2""-quinquethiophene (IV-a-2) was produced from 5-bromo-5"-ethyl-2,2':5',2"-terthiophene (2.13 g, 6 mmol), Pd(PPh$_3$)$_4$ (350 mg, 0.3 mmol) and 4,4,5,5-tetramethyl-2-[5'-(10-undecenyl)-2,2'-bithien-5-yl]-1,3,2-dioxaborolane (I-a) (3.11 g, 7 mmol) as described in Example 2 in 40 ml of anhydrous toluene and 10 ml of a 2 M aqueous Na$_2$CO$_3$ solution. After recovery as in Example 2, the organic phase was filtered through a G4 glass filter and the orange precipitate was recrystallised in toluene. Yield: 2.96 g (83% of theoretical) of dark orange powder (I-a-1.2).

FD MS analysis: M.$^+$ 100%, m/e=592.1

$^1$H NMR (CDCl$_3$, TMS/ppm): 1.23–1.44 (overlapped peaks with max. at 1.290, 15 H, including t at 1.329 ppm, J=7.3, 3H), 1.682 (m, J=7.5, M=5, 2H), 2.041 (q, J=7.0, 2H), 2.791 (t, J=7.6, 2H), 2.841 (q, J=7.6, 2H), 4.930 (d, J=10.3, 1H), 4.989 (d, J=17.1, 1H), 5.813 (m, 1H), 6.684 (d, J=3.9, 1H), 6.704 (d, J=3.4, 1H), 6.99 (overlapped peaks, 4H), 7.048 (d, J=3.4, 2H), 7.053 (s, 2H).

Melt behaviour (° C.): K 240 N 242 I (K=crystalline, N=nematic liquid crystalline, I=isotropic liquid).

Example 4

Production of 5-ethyl-5'''-(11-triethoxysilylundecyl)-2,2':5',2":5",2'''-quaterthiophene (I-a-2.1)

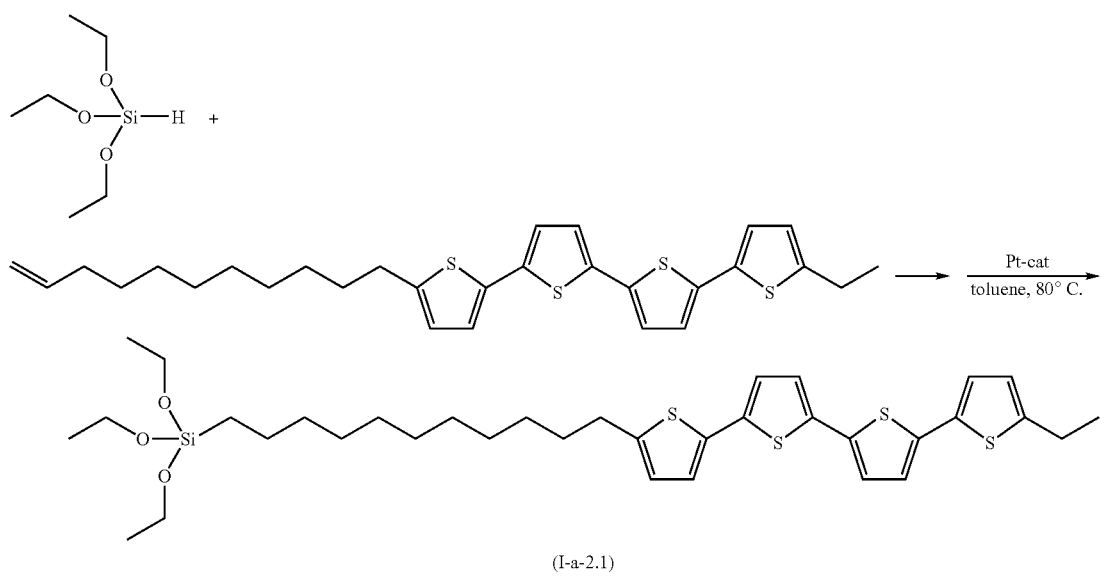

(I-a-2.1)

5-Ethyl-5'''-(10-undecenyl)-2,2':5',2":5",2'''-quaterthiophene (I-a-1.1) from Example 2 (410 mg, 0.8 mmol) was placed in a 100 ml multinecked flask with condenser, gas outlet, thermometer and septum adapter and flooded with nitrogen. 15 ml of anhydrous toluene were then added and the mixture heated to 80° C. until everything (I-a-1.1) was dissolved. Triethoxysilane (324 mg, 2 mmol) and a solution of a platinum cyclovinyl methyl siloxane complex of cyclic methyl vinyl siloxanes (3–3.5 wt. % Pt, 5 ml, obtainable via ABCR for example) were added one at a time by injection at 80° C. The mixture was stirred for 20 hours at 80° C. and after cooling the solvent was then removed in a rotary evaporator. The solid, yellow product obtained was filtered over silica gel in toluene. Yield: 151 mg (27% of theoretical) of yellow powder (I-a-2.1).

FD MS analysis: M.$^+$ 100%, m/e=674.2.

$^1$H NMR (CDCl$_3$, TMS/ppm): 0.628 (t, J=8.1 Hz, 2H), 1.225 (t, J=7.1 Hz, 9H), 1.23–1.44 (overlapped peaks with max. at 1.267, 21 H, including t at 1.327 ppm, J=7.6 Hz, 3H), 1.678 (m, J=7.3, M=5, 2H), 2.788 (t, J=7.6 Hz, 2H), 2.839 (q, J=8.3 Hz, 2H), 3.814 (q, J=6.9 Hz, 6H), 6.680 (d, J=3.4 Hz, 1H), 6.700 (d, J=3.4 Hz, 1H), 6.98 (overlapped peaks, 4H), 7.030 (d, J=3.9 Hz, 2H)

Melt behaviour (° C.): K 160 I (K=crystalline, I=isotropic liquid).

Example 5

Production of 1-[11-(5'''-ethyl-2,2':5',2'':5'',2'''-quaterthien-5-yl)undecyl]-1,1,3,3-tetramethyl disiloxane (I-a-3.1)

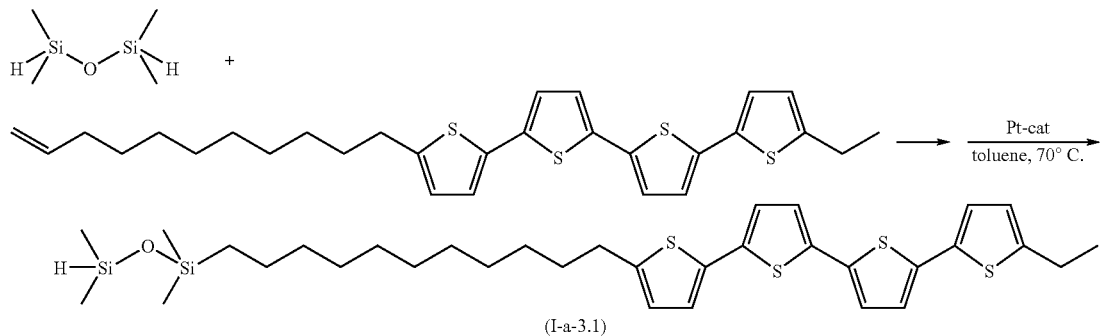

(I-a-3.1)

1-[11-(5'''-Ethyl-2,2':5',2'':5'',2'''-quaterthien-5-yl)undecyl]-1,1,3,3-tetramethyl disiloxane (I-a-3.1) was produced from 5-ethyl-5'''-(10-undecenyl)-2,2':5',2'':5'',2'''-quaterthiophene (I-a-1.1) (1.79 g, 3.5 mmol), 1,1,3,3-tetra-methyldisiloxane (25 ml, 18.8 g, 140 mmol) and a solution of a platinum cyclovinyl methyl siloxane complex of cyclic methyl vinyl siloxanes (3–3.5 wt. % Pt, 10 ml) as described in Example 4 in 70 ml of anhydrous toluene at 70° C. and purified. Yield: 2.26 g (94% of theoretical) of yellow powder (I-a-3.1).

FD MS analysis: M.$^+$ 99+%, m/e=644.0

$^1$H NMR (CDCl$_3$, TMS/ppm): 0.056 (s, 6H), 0.160 (d, J=2.5 Hz, 6H), 0.527 (t, J=7.6 Hz, 2H), 1.23–1.43 (overlapped peaks with max. at 1.267, 21 H, including t at 1.326 ppm, J=7.8 Hz, 3H), 1.680 (m, J=7.5, M=5, 2H), 2.789 (t, J=7.6 Hz, 2H), 2.840 (q, J=7.2 Hz, 2H), 4.676 (m, J=2.8 Hz, M=7, 1H), 6.679 (d, J=3.4 Hz, 1H), 6.699 (d, J=3.4 Hz, 1H), 6.98 (overlapped peaks, 4H), 7.029 (d, J=3.9 Hz, 2H).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A compound represented by the following formula (I), $$X\!-\!R^1\text{-}[Ar]_n\text{-}R^2 \quad (I)$$

wherein, n is a whole number from 4 to 10,

Ar is, independently for each n, a member selected from the group consisting of 1,4-phenylene, substituted 1,4-phenylene, 2,7-fluorenylene, substituted 2,7-fluorenylene, 2,5-thienylene, substituted 2,5-thienylene, 1,2-ethenylene and substituted 1,2-ethenylene, wherein the substituents of the substituted 1,4-phenylene, substituted 2,7-fluorenylene, substituted 2,5-thienylene and substituted 1,2-ethenylene are each independently selected from at least one member of the group consisting of hydrogen, linear or branched $C_1$–$C_{20}$ alkyl radicals and linear or branched $C_1$–$C_{20}$ alkyl radicals interrupted by at least one O atom, $R^1$ is selected from the group consisting of $C_3$–$C_{30}$ alkylene group, $C_3$–$C_{30}$ alkylene group interrupted by at least one O atom, $C_3$–$C_{30}$ alkylene group interrupted by at least one S atom, silylene groups, phosphonoyl groups, and phosphoryl groups, $R^2$ is selected from the group consisting of H, a linear or branched $C_1$–$C_{20}$ alkyl group, a linear $C_1$–$C_{20}$ alkyl group interrupted by at least one O atom, a linear $C_1$–$C_{20}$ alkyl group interrupted by at least one S atom, silylene groups, phosphonoyl groups and phosphoryl groups, and X is selected from the group consisting of vinyl, chlorine, iodine, hydroxyl, alkoxy group having 1 to 3 carbon atoms, alkoxysilyl, silyl, chlorosilyl, siloxane, hydroxy, carboxy, methyl carbonate, ethyl carbonate, aldehyde, methyl carbonyl, amino, amido, sulfone, sulfonic acid, halosulfonyl, sulfonate, phosphonic acid, phosphonate, trichloromethyl, tribromomethyl, cyanate, isocyanate, thiocyanate, isothiothiocyanate, cyano and nitro group.

2. The compound of claim 1 wherein Ar is selected, independently for each n, from the group consisting of 2,5-thienylene and substituted 2,5-thienylene.

3. The compound of claim 1 wherein X is selected from the group consisting of alkoxysilyl and siloxane.

4. The compound of claim 1 wherein X is a vinyl group.

5. A process for producing the compound of claim 1 comprising reacting, by means of Suzuki coupling, (i) an organoboron compound with,
(ii) at least one halide compound selected from the group consisting of aryl halide and heteroaryl halide.

6. The process of claim 5 wherein said organoboron compound (i) is represented by the following formula (II),

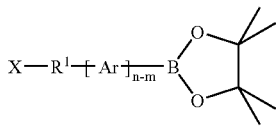 (II)

wherein n, Ar, $R^1$ and X are as described in claim 1, and m stands for a whole number from 1 to 5,
and said halide compound (ii) is represented by the following formula (III),

 (III)

wherein m and Ar are as described for formula (II),
R is as described in formula (I) of claim 1, and
Y is selected from the group consisting of Cl, Br, I and —O—$SO_2R^3$, wherein $R^3$ is selected from the group consisting of methyl, trifluoromethyl, phenyl and tolyl.

7. A process for producing the compound of claim 3, comprising:
(i) providing an intermediate compound represented by formula (I),
wherein X is a vinyl group; and
(ii) hydrosilylating said intermediate compound, thereby forming the compound of claim 3.

8. An electronic component comprising at least one semi-conductive layer comprising said compound of claim 1.

9. An electronic component of claim 8, in which the compound of claim 1 forms a mono layer having the function of a dielectric layer and of a semiconductive layer.

10. A self-assembled molecule (SAM molecule layer) comprising the compound of claim 1.

11. A self-assembled molecule layer of claim 10, in which the compound of claim 1 forma a mono layer having the function of a dielectric layer and of a semiconductive layer.

12. A semiconductive layer comprising the compound of claim 1.

* * * * *

UNITED STATES PATENT AND TRADEMARK OFFICE
CERTIFICATE OF CORRECTION

PATENT NO. : 7,196,206 B2  Page 1 of 1
APPLICATION NO. : 10/984512
DATED : March 27, 2007
INVENTOR(S) : Stephan Kirchmeyer et al.

It is certified that error appears in the above-identified patent and that said Letters Patent is hereby corrected as shown below:

On the Title Page: item (56);

In the References Cited, "Michalitsch, R. et al: "A practical synthesis of functionalized alkyl-oligothiophenes for molecular self-assembly" Journal of Heterocyclic Chemistry, 39 (3) 649-653 Coden: JHTCAD; ISSN: 0022-152X, 2001, XP002316604." should read -- Michalitsch, R. et al: "A practical synthesis of functionalized alkyl-oligothiophenes for molecular self-assembly" Journal of Heterocyclic Chemistry, 38 (3) 649-653 Coden: JHTCAD; ISSN: 0022-152X, 2001, XP002316604."--.

In the References Cited, "J. Phys. Chem. B, 101, (month unavalabl) 1997, pp. 5951-5962, B. Liedberg et al, "Self-Assembly of α-Functionalized Terthiophenes on Gold". should read -- "J. Phys. Chem. B, 101, (month unavalable) 1997, pp. 5951-5962, B. Liedberg et al, "Self-Assembly of α-Functionalized Terthiophenes on Gold".--.

Signed and Sealed this

Sixteenth Day of October, 2007

JON W. DUDAS
*Director of the United States Patent and Trademark Office*